United States Patent
Kullik et al.

(10) Patent No.: US 6,895,962 B2
(45) Date of Patent: May 24, 2005

(54) DEVICE FOR SUPPORTING RESPIRATION

(75) Inventors: Götz Kullik, Lübeck (DE); Hans-Ulrich Hansmann, Barnitz (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 10 days.

(21) Appl. No.: 10/306,699

(22) Filed: Nov. 27, 2002

(65) Prior Publication Data

US 2003/0172930 A1 Sep. 18, 2003

(30) Foreign Application Priority Data

Mar. 12, 2002 (DE) .......................................... 102 10 878

(51) Int. Cl.$^7$ ................................................. A62B 7/00
(52) U.S. Cl. ............................... 128/204.18; 4/204.21; 4/204.22; 4/204.23
(58) Field of Search ....................... 128/205.12, 205.29, 128/205.27, 206.17, 206.21, 206.28, 204.18, 204.21, 204.22, 204.23, 204.26

(56) References Cited

U.S. PATENT DOCUMENTS

| | | | | |
|---|---|---|---|---|
| 3,840,006 A | * | 10/1974 | Buck et al. ............. | 128/204.21 |
| 4,320,755 A | * | 3/1982 | Flint et al. ............. | 128/205.12 |
| 4,590,951 A | | 5/1986 | O'Connor | |
| 4,905,686 A | | 3/1990 | Adams | |
| 5,111,809 A | * | 5/1992 | Gamble et al. ......... | 128/204.18 |
| 5,303,701 A | * | 4/1994 | Heins et al. ............ | 128/206.17 |
| 5,413,097 A | * | 5/1995 | Birenheide et al. ..... | 128/206.17 |
| 5,865,174 A | * | 2/1999 | Kloeppel ................ | 128/204.23 |
| 5,868,133 A | * | 2/1999 | DeVries et al. ........ | 128/204.21 |
| 6,050,262 A | * | 4/2000 | Jay ........................ | 128/205.27 |
| 6,418,927 B1 | | 7/2002 | Kullik | |
| 6,474,960 B1 | | 11/2002 | Hansmann | |
| 6,526,970 B2 | | 3/2003 | DeVries et al. | |
| 6,637,433 B2 | * | 10/2003 | Schob .................... | 128/204.19 |
| 6,705,314 B1 | * | 3/2004 | O'Dea .................... | 128/204.18 |
| 6,705,315 B2 | * | 3/2004 | Sullivan et al. ........ | 128/204.18 |

FOREIGN PATENT DOCUMENTS

| | | |
|---|---|---|
| DE | 42 02 025 | 7/1993 |
| DE | 41 33 235 | 9/1993 |
| EP | 0 164 946 A2 | 12/1985 |
| EP | 0 164 946 | 12/1985 |

* cited by examiner

*Primary Examiner*—Henry Bennett
*Assistant Examiner*—Amanda Wieker
(74) *Attorney, Agent, or Firm*—McGlew and Tuttle, P.C.

(57) ABSTRACT

A compact device for supporting respiration is provided making possible a mobile, autonomous, pressure-supported respiration of patients near the lungs with very small dead spaces and flow resistances. The device is especially useful for medical applications. The device includes a rotary compressor (3) with an electric drive motor provided with a filter (7) arranged directly upstream in the direction of flow. The compressor (3) is arranged directly upstream of a breathing mask (2) or a breathing tube. A control unit (6) is provided for setting respiration pressure on a basis of speed of rotation. The control unit (6) is connected to the drive motor of the compressor (3).

25 Claims, 1 Drawing Sheet

DEVICE FOR SUPPORTING RESPIRATION

FIELD OF THE INVENTION

The present invention pertains to a device for supporting respiration

BACKGROUND OF THE INVENTION

Such a device has become known from U.S. Pat. No. 6,050,262. This prior-art device has a gas mask with a connected gas filter, to which ambient air is admitted by means of an upstream fan in order to facilitate the respiration of the mask user. The fan is driven by means of an electric motor.

SUMMARY OF THE INVENTION

The object of the present invention is to provide an improved device for supporting ventilation, which also makes possible respiration with different respiration pressures directly at or in the access to the lungs in medical practice.

According to the invention, a device for respiration support is provided with a rotary compressor with an electric drive motor. The device is also provided with a filter arranged directly upstream in a direction of flow. The compressor is arranged directly upstream of a breathing mask or a breathing tube. A control unit is provided for setting the respiration pressure on the basis of the speed of rotation of the rotary compressor and is connected to the drive motor of the compressor.

An important advantage of the present invention arises from the compact design of the battery-operated device portable on the body of the person being respirated with the rotary compressor used as the pressure source for the breathing air, which brings about an increase in the pressure by imparting momentum to the gas being delivered. The rotary compressor is designed as a radial, axial, drum-type or cross flow compressor directly connected to a breathing mask or to a breathing tube and without connection lines or tubes, so that the support of respiration or respiration is possible directly at or in the access to the lung. In addition, different respiration pressures can be set rapidly if necessary either according to preset, selected pressure stages or in a time-dependent manner, corresponding to stored respiration pressure curves, i.e., especially with an intermittent respiration pressure curve, which is set in a highly dynamic manner solely on the basis of the speed of rotation of the compressor used with small moving masses.

An especially preferred embodiment of the present invention has a respiratory flow sensor in the breathing mask, which is electrically connected to the control unit, so that the control unit is actuated as a function of the measured signals of the respiratory flow sensor and the speed of rotation of the compressor and consequently the resulting respiration pressure for the patient or the breathing-supported person is changed highly dynamically, without a delay due to line losses. The filter, which is arranged directly upstream of the compressor and is detachably placed thereon, consists of a nonwoven or fiber material and is especially a cellulose filter that is highly effective for particle retention, including microorganisms, which is also used at the same time for sound absorption from the compressor, so that use near the patient is possible without adverse subjective effects. For respiration support, air is drawn by the compressor from the environment through the filter arranged directly upstream and is delivered under pressure into the breathing mask or alternatively into a breathing tube.

The compact and lightweight design of the battery-operated device according to the present invention makes possible the mobile, autonomous use of the device directly at the patient to be respirated for pressure-supported respiration with very small dead spaces and flow resistances in the path of the breathing gas. The weight of such a device for a nasally arranged breathing mask is about 100 g with dimensions of about 50 mm of edge length.

The breathing gas may be optionally conditioned in a patient-specific manner in the area of the breathing mask by means of a heater and the simultaneous feeding of humidified air and/or another auxiliary gas, e.g., oxygen or nitrogen monoxide. Furthermore, provisions are optionally made for feeding a drug aerosol or an anesthetic for the treatment of the patient.

A pressure increase generated is very extensively independent from the gas volume flow being delivered, especially for a radial compressor, so that the patient being respirated does not experience any substantial change in the respiration parameters as a function of an untightness of the breathing mask and an associated, often unavoidable leakage, which is another advantage of the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
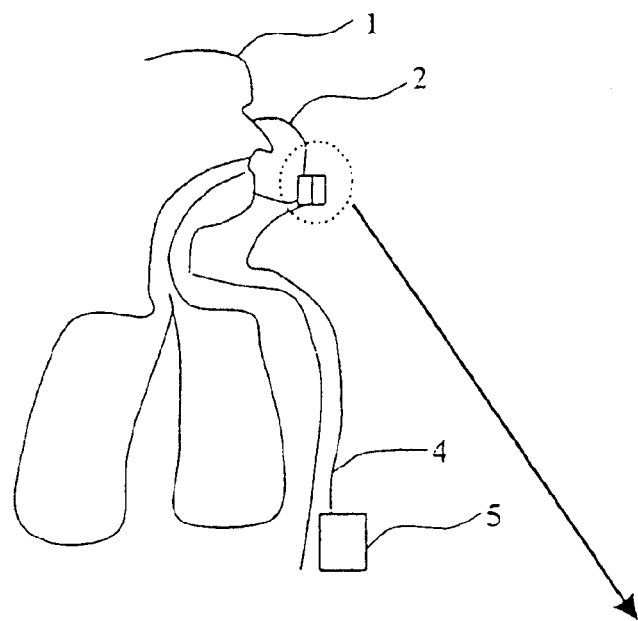
FIG. 1 is a schematic view of a mobile device for respiration support to be carried on the body of a person, e.g., a freely moving patient.
Figure 2:
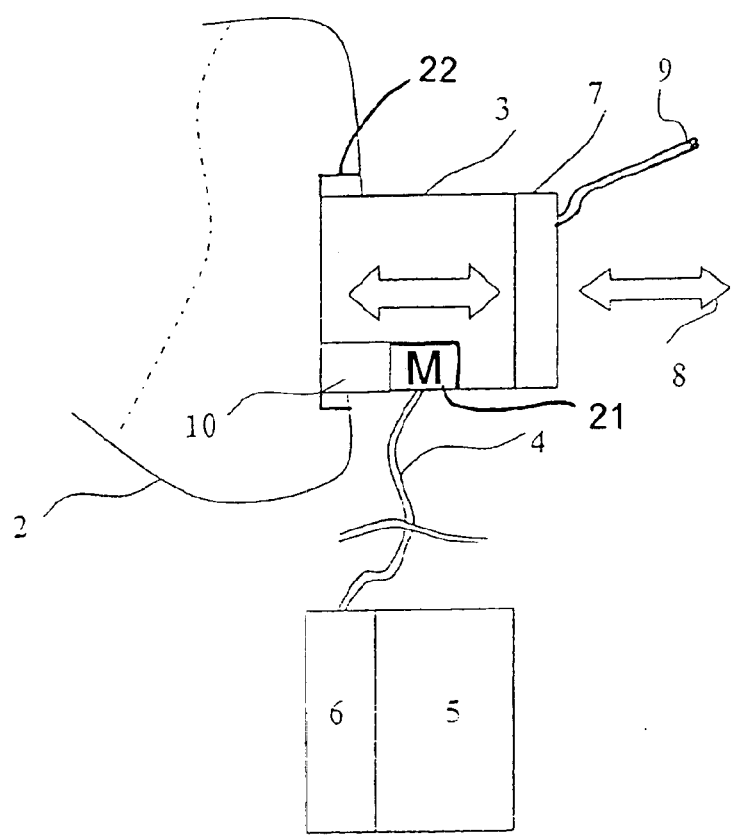
FIG. 2 is an enlarged detail of the individual components of the device in its right-hand part.

Referring to the drawings in particular, an exemplary embodiment of the present invention is shown in FIG. 1 as a mobile device for respiration support to be carried on the body of a person, e.g., a freely moving patient 1. FIG. 2 shows an enlarged detail of the individual components of the device in its right-hand part. A very compact rotary compressor 3, which is in direct flow connection with a breathing mask 2 (or other user interface part such as a breathing tube without connection lines) and is detachably connected to same as one assembly unit, is used as the pressure source. The rotary compressor 3 is especially a radial compressor, but may also be designed as an axial, drum-type or cross flow compressor.

All four compressors 3 mentioned as "rotary compressors" (designed as a radial compressor, as an axial compressor, as a drum-type compressor or as a cross flow compressor) belong to the group of the dynamic type compressors, which bring about the pressure increase in a gas being delivered by imparting momentum. The blades or vanes of the compressor 3 transmit a rotational impulse to the gas molecules flowing through corresponding to the speed of rotation, and the transmitted energy is converted due to the design into gas velocity and gas pressure in different manners.

The rotary compressor 3 is provided with a compressor wheel with a diameter of less than 40 mm and with an electric drive motor 21 in a very compact form as one assembly unit, which is connected to the breathing mask 2. Batteries or rechargeable batteries are used as the energy source 5. The energy and optionally signals are transmitted by means of the electric connection 4. The rotary compressor 3 has sufficiently large gas flow cross sections of at least 75 mm$^2$ for the breathing gases and generates the gas pressures of up to 5,000 Pa needed for pressure-supported respiration. Both the electric drive and the compressor wheel have a very low inertia of the rotating masses, totaling at most 2 g×cm$^2$. The breathing gases are delivered into the breathing mask 2 through a filter 7 made of paper fibers for particles and microorganisms from the ambient air 8, which said filter is arranged directly upstream of the rotary compressor 3, and auxiliary gas lines 9, carrying gases such as oxygen or nitrogen monoxide, are optionally added, and the gases are thus available to the patient 1 directly at the access to the lungs. The filter 7 is also used at the same time for sound absorption of sound emissions from the rotary compressor 3 and it improves the comfort of wear directly at the patient 1 as a result.

The rotary compressor 3 generates the pressure increase necessary for the respiration support in the breathing mask 2 due to the impartation of momentum to the breathing gas as a function of the circumferential velocity of the compressor wheel of the rotary compressor 3. Due to the low inertia of the rotating masses of the radial compressor used, the speed of rotation and consequently also the respiration pressure can be changed so rapidly by means of a control unit 6 that the device can follow the spontaneous breathing efforts of the patient 1. Due to the low inertia of masses of the moving components, the energy consumption for the acceleration is so small that a mobile, autonomous use at the patient 1 is possible with a small energy storage unit 5 and electric connection 4 to the rotary compressor 3 for the pressure-supported respiration of the patient. The rotary compressor 3 makes possible deep breathing in both directions to the ambient air 8 corresponding to the double arrows shown, so that a separate expiration valve does not necessarily have to be present in or at the breathing mask 2.

A respiratory flow sensor 10, which is designed especially as a pressure sensor and transmits measured signals to the control unit 6 via the electric connection 4, is optionally located in the breathing mask 2 in the path of the gas flow. As a result, the control unit 6 is actuated as a function of the measured signals of the respiratory flow sensor 10 and the speed of rotation of the rotary compressor 3 and consequently the resulting respiration pressure for the patient 1 are changed highly dynamically, without a delay due to line losses.

The compact and lightweight design of the device according to the present invention makes possible the mobile, autonomous use of the device directly at the patient 1 to be respirated for pressure-supported respiration with very small dead spaces and flow resistances in the path of the breathing gas. The mass of such a device is about 100 g with dimensions of about 50 mm (edge length) for the drive unit with the compressor wheel. Depending on the particular embodiment of the device, different respiration pressures are set either only according to preset, fixed pressure stages or changed in a time-dependent manner corresponding to the respiration pressure curves stored in the control unit 6, i.e., especially with an intermittent respiration pressure curve, which enables the patient 1 to breath out independently and is set highly dynamically solely on the basis of the variable speed of rotation of the rotary compressor 3 used, which has small moving masses, as a function of the measured signals of the respiratory flow sensor 10, which are received by the control unit 6. In the simplest case, the control unit 6 is used only to set a permanently preset respiration pressure or one of several selectable respiration pressures on the basis of the speed of rotation of the drive motor and of the driven compressor wheel of the compressor 3, which speed is constant for a given respiration pressure.

While a specific embodiment of the invention has been shown and described in detail to illustrate the application of the principles of the invention, it will be understood that the invention may be embodied otherwise without departing from such principles.

What is claimed is:

1. A device for respiration support, the device comprising:
   a rotary compressor with an electric drive motor;
   a filter arranged directly upstream of the rotary compressor with no intermediary with respect to a direction of gas flow;
   a user interface part including one of a breathing mask and a breathing tube, the compressor being arranged directly upstream of said breathing mask or breathing tube with no intermediary with respect to a direction of gas flow; and
   a control unit for setting a respiration pressure on the basis of the speed of rotation of said rotary compressor, said control unit being connected to said drive motor.

2. A device in accordance with claim 1, wherein said rotary compressor is one of a radial compressor, an axial compressor, a drum-type compressor or a cross flow compressor.

3. A device in accordance with claim 1, wherein a speed-dependant or time-dependent respiration pressure curve is used by said control unit to set said speed of rotation of said drive motor of said compressor, said speed-dependent or time-dependent respiration pressure curve being stored in said control unit.

4. A device in accordance with claim 1, further comprising a respiratory flow sensor connected to said control unit and arranged in said user interface part, said control unit being actuated as a function of measured signals of said respiratory flow sensor.

5. A device in accordance with claim 1, wherein said filter consists of a nonwoven or fiber material.

6. A device in accordance with claim 1, wherein said tube is an endotracheal tube or a tracheometry tube.

7. A device in accordance with claim 1, further comprising a feed line for feeding an auxiliary gas or an aerosol simultaneously with ambient air, said feed line being provided in an inflow area of said compressor facing away from a high pressure side.

8. A device in accordance with claim 4, wherein said respiratory flow sensor is a pressure sensor with a measuring transducer containing a piezo crystal or a strain gauge.

9. A device in accordance with claim 1, wherein said breathing mask is provided with a heating means.

10. A device in accordance with claim 1, wherein said device is adapted to be connected to a patient for mobile, autonomous, pressure-supported patient respiration in medicine.

11. A method of respiration support, the method comprising:
   providing a rotary compressor with an electric drive motor;
   providing a user interface part including one of a breathing mask and a breathing tube;
   arranging a filter directly upstream of the rotary compressor with no intermediary between said compressor and said user interface with respect to a direction of gas flow;

arranging the compressor directly upstream of said breathing mask or breathing tube with no intermediary between said compressor and said user interface with respect to the gas flow; and controlling a respiration pressure on the basis of the speed of rotation of the rotary compressor with a control unit connected to the drive motor.

12. A method in accordance with claim 11, wherein said rotary compressor is provided as one of a radial compressor, an axial compressor, a drum-type compressor or a cross flow compressor.

13. A method in accordance with claim 11, wherein a speed-dependant or time-dependent respiration pressure curve is used by the control unit to set a speed of rotation of the drive motor of the compressor and the speed-dependent or the time-dependent respiration pressure curve is stored in the control unit.

14. A method in accordance with claim 11, further comprising providing a respiratory flow sensor connected to the control unit and arranged in the user interface part, the control unit being actuated as a function of said measured signals of said respiratory flow sensor.

15. A method in accordance with claim 11, wherein said filter is formed of a nonwoven or fiber material.

16. A method in accordance with claim 11, wherein the breathing tube is provided as an endotracheal tube or a tracheometry tube.

17. A method in accordance with claim 11, further comprising providing a feed line and using the feed line for feeding an auxiliary gas or an aerosol simultaneously with ambient air, said feed line being provided in said inflow area of said compressor facing away from a high pressure side.

18. A method in accordance with claim 11, wherein said respiratory flow sensor is a pressure sensor with a measuring transducer containing a piezo crystal or a strain gauge.

19. A method in accordance with claim 11, wherein said breathing mask is provided with a heating means.

20. A method in accordance with claim 11, further comprising connecting each of the rotary compressor with the electric drive motor and the filter arranged directly upstream of the rotary compressor with respect to a direction of flow and the control unit to a patient for mobile, autonomous, pressure-supported patient respiration.

21. A respiration support apparatus, the apparatus comprising:

a rotary compressor actuated by an electric drive motor;

a filter arranged directly upstream of said rotary compressor with no intermediary with respect to a direction of gas flow;

a user interface part including one of a breathing mask, an endotracheal tube, a tracheometry tube, and a truncated tubular mouthpiece, said compressor being arranged directly upstream of said user interface part with no intermediary with respect to a direction of gas flow.

22. A method of delivering a gas flow to a user, the method comprising:

providing a user interface part including one of a breathing mask, an endotracheal tube, a tracheometry tube, and a truncated tubular mouthpiece;

providing a compressor connected directly to said user interface part with no intermediary between said compressor and said user interface with respect to the gas flow;

providing a filter connected directly to said compressor with no intermediary between said compressor and said user interface with respect to the gas flow; and providing a gas through said filter, said compressor, and through said user interface to the user.

23. A method in accordance with claim 22, the method further comprising:

adapting said user interface to be connected to a patient for mobile, autonomous, pressure-supported patient respiration in medicine.

24. A respiration support apparatus according to claim 21, said apparatus further comprising:

a control unit for setting a respiration pressure on the basis of the speed of rotation of said rotary compressor, said control unit being connected to said electric drive motor;

a respiratory flow sensor connected to said control unit and arranged in said user interface part, said control unit being actuated as a function of measured signals of said respiratory flow sensor.

25. A method according to claim 22, said method further comprising:

providing a rotary compressor with an electric drive motor;

controlling a respiration pressure on the basis of the speed of rotation of said compressor with a control unit connected to said electric drive motor;

providing a respiratory flow sensor connected to said control unit and arranged in said user interface part, wherein said control unit is actuated as a function of measured signals of said respiratory flow sensor.

* * * * *